(12) United States Patent
Peng et al.

(10) Patent No.: US 9,744,146 B2
(45) Date of Patent: Aug. 29, 2017

(54) METHOD FOR ALLEVIATING DISTURBANCE OF BILE ACID METABOLISM, AMINO ACID METABOLISM, AND/OR GUT MICROBIOTA METABOLISM

(71) Applicant: China Medical University, Taichung (TW)

(72) Inventors: Wen-Huang Peng, Taichung (TW); Li-Heng Pao, Taichung (TW); Jung Chao, Taichung (TW); Hao-Yuan Cheng, Taichung (TW); Meng-Shiou Lee, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 0 days.

(21) Appl. No.: 14/529,313

(22) Filed: Oct. 31, 2014

(65) Prior Publication Data
US 2015/0174087 A1    Jun. 25, 2015

(30) Foreign Application Priority Data
Dec. 25, 2013 (TW) .............................. 102148166 A

(51) Int. Cl.
*A61K 31/192*     (2006.01)
*A23L 33/105*    (2016.01)
*A61K 31/216*    (2006.01)

(52) U.S. Cl.
CPC .......... *A61K 31/192* (2013.01); *A23L 33/105* (2016.08); *A61K 31/216* (2013.01)

(58) Field of Classification Search
None
See application file for complete search history.

(56) References Cited

U.S. PATENT DOCUMENTS

2003/0096050 A1* 5/2003 Inaoka .................. A21D 2/145
                                                          426/597

FOREIGN PATENT DOCUMENTS

WO    WO 2006/048457    *    5/2011    .............. A61P 31/04

OTHER PUBLICATIONS

Kolter et al. (Gastroenterol Hepatol (N Y). Feb. 2010; 6(2): 117-119).*
Tzipori et al. (Gut 1985;26:570-578 doi:10.1136/gut.26.6.570).*
Y.-J. Ahn et al., "Growth-inhibitory effects of Galla Rhois-derived tannins on intestinal bacteria" Journal of Applied Microbiology 1998, 84, 439-443.
Xiaohuo Shi et al., "Gallic Acid Intake Induces Alterations to Systems Metabolism in Rats" J. Proteome Res. 2013, 12, 991-1006.
Mariana V. Machado and Helena Cortez-Pinto, "Gut microbiota and nonalcoholic fatty liver disease" Annals of Hepatology, July-August, vol. 11 No. 4, 2012: 440-449.
Kitzman et al. "Non-invasive whole genome sequencing of a human fetus" Sci Transl Med. Jun. 6, 2012; 4(137): 137ra76.doi:10.1126/scitranslmed.3004323.
June L. Round and Sarkis K. Mazmanian, "The gut microbiome shapes intestinal immune responses during health and disease" Nat Ref Immunol. May 2009; 9(5):313-323. doi:10.1038/nri2515.
Clemente et al. "The Impact of the Gut Microbiota on Human Health: An Integrative View" Cell 148, Mar. 16, 2012, pp. 1258-1270.
Teruo Miyazaki and Yasushi Matsuzaki, "Taurine and liver diseases: a focus on the heterogeneous protective properties of taurine" Amino Acids (2014) 46:101-110.
Rare Disease Diet Control Manual-amino acid metabolism, Foundation for Rare Disorders, p. 18, 22 and 26-31 (and its English translation).

* cited by examiner

*Primary Examiner* — Kortney L Klinkel
*Assistant Examiner* — William Lee
(74) *Attorney, Agent, or Firm* — McClure, Qualey & Rodack, LLP

(57) ABSTRACT

A method for alleviating at least one of the disturbance of bile acid metabolism, the disturbance of amino acid metabolism, and the disturbance of gut microbiota metabolism in a subject, comprising administering to the subject a composition or a health food comprising an active component selected from the group consisting of gallic acid, a pharmaceutically acceptable salt of gallic acid, a pharmaceutically acceptable ester of gallic acid, and combinations thereof.

6 Claims, 2 Drawing Sheets
(2 of 2 Drawing Sheet(s) Filed in Color)

METHOD FOR ALLEVIATING DISTURBANCE OF BILE ACID METABOLISM, AMINO ACID METABOLISM, AND/OR GUT MICROBIOTA METABOLISM

CROSS-REFERENCE TO RELATED APPLICATIONS

Not applicable.

BACKGROUND OF THE INVENTION

Field of the Invention

The present invention relates to a use of gallic acid (GA) and its pharmaceutically acceptable salt and ester, especially in healthcare. In particular, the present invention relates to a method for alleviating at least one of the disturbance of bile acid metabolism, disturbance of amino acid metabolism and disturbance of gut microbiota metabolism by using a gallic acid and/or a pharmaceutically acceptable salt and/or ester of gallic acid.

Description of the Related Art

Gallic acid, also known as wubeizi acid or bei acid, is a natural polyphenolic compound that exists in various parts of natural plants. For example, it is found in the root and the stem of *Rheum palmatum* L. in Polygonaceae, the leaves of *Eucalyptus robusta* Smith in Myrtaceae, the fruit of *Cornus officinalis* Sieb. et Zucc in Cornaceae, the flower of *Lythrum salicaria* Linn. in Lythraceae, the leaves of *Coriaria intermedia* Matsum. in Coriariaceae, the pericap of *Punica granatum* L. in Punicaceae, etc. Gallic acid has low toxicity and good safety and its No Observed Adverse Effect Level (NOAEL) in a mouse is greater than 5000 mg/kg. Also, gallic acid shows no negative response in rat toxicological research. Therefore, gallic acid has a high potential for development. It has been known that Gallic acid has various biological activities, such as anti-oxidation, anti-inflammatory, anti-tumor, obesity control, liver protection, etc., while the mechanisms of such activities are still unclear.

The diet, trophic structure and lifestyle of people in modern society are undergoing tremendous changes, and the morbidity of hypertension, hyperlipidemia, atherosclerosis, tumor and other metabolic disorders have also increased. Researches have found that in the proceeding of these diseases, the biochemistry metabolism in organism would change, such as the occurrence of the disturbance of amino acid metabolism. The previous studies have found that in the proceeding of the above diseases, the occurrence of the disturbance of amino acid metabolism is correlated to and has causal relationship with the diseases. That is, one single metabolic disease could develop into a variety of coexisting diseases. Therefore, it will be a significant benefit for the above diseases if the disturbance of amino acid metabolism can be alleviated.

The disturbance of bile acid metabolism is also a cause for a lot of diseases. Bile acid, a general designation of 24-carbons cholanic hydroxyl derivatives, is a major solid component of bile, and is an endogenous organic anion. There are fifteen (15) kinds of bile acid in human bile, comprising primarily cholic acid, chenodeoxycholic acid, deoxycholic acid, small amounts of lithocholic acid and trace amounts of ursodeoxycholic acid. Bile acid is the major permeating active material with a function of cholagogue, and can increase the secretion and elimination of bile. It plays a role of anti-microbes in the bile duct and intestine and in preventing the bacterial overgrowth in bile duct and intestine and the shift of enteric microflora. If the disturbance of bile acid metabolism occurs in a human body, it will result in the appearance of associated diseases such as cholestasis liver diseases, cholestasis, bile duct infection, bile duck stones, congenital bile duct diseases, etc.

In addition, in a normal human body, there is a certain balance between the enteric microflora and the host in the gastrointestinal tract. The enteric microflora in human gastrointestinal tract serve various important functions such as promoting digestion, increasing nutrition, regulating immunity, inhibiting the proliferation of harmful microbe, anti-tumor, anti-aging, etc. The related studies have indicated that if the relationship between the enteric microflora and the host is imbalance, it will result in associated diseases such as aging, inflammatory enteritis, depression disorder, anxiety disorder, immune disorder, allergy, etc (see Ann Hepatol. 2012 July-August; 11(4):440-9., Sci Transl Med. 2012 Jun. 6; 4(137):137, Nat Rev Immunol. 2009 May; 9(5):313-23. Cell. 2012 Mar. 16; 148(6):1258-70, which is entirely incorporated hereinto by reference). Therefore, the intestine microbe is becoming an important target of a new medicament in recent years. If the disturbance of the enteric microflora can be alleviated, the progression of the above diseases could be ameliorated.

For the above metabolic mechanisms, the inventors of the present invention found that gallic acid has the effects of alleviating the disturbance of metabolism, such as alleviating the disturbance of bile acid metabolism, the disturbance of amino acid metabolism and/or the disturbance of gut microbiota metabolism in the diseased body. Therefore, in addition to helping with metabolism, gallic acid can be used for daily health care.

SUMMARY OF THE INVENTION

An objective of the present invention is to provide a method for alleviating at least one of the disturbance of bile acid metabolism, disturbance of amino acid metabolism, and disturbance of gut microbiota metabolism in a subject, comprising administering to the subject a composition comprising an active component selected from the group consisting of gallic acid, a pharmaceutically acceptable salt of gallic acid, a pharmaceutically acceptable ester of gallic acid, and combinations thereof. Preferably, the method is for treating the diseases related to the disturbance of bile acid metabolism, such as a cholestatic liver disease, cholestasis, bile duct infection, bile duct stone, and a congenital bile duct disease.

Another objective of the present invention is to provide a method for alleviating at least one of the disturbance of bile acid metabolism, the disturbance of amino acid metabolism, and the disturbance of gut microbiota metabolism in a subject, comprising administering to the subject a health food comprising an active component selected from the group consisting of gallic acid, a pharmaceutically acceptable salt of gallic acid, a pharmaceutically acceptable ester of gallic acid, and combinations thereof. Preferably, the method is for alleviating the disturbance of bile acid metabolism, and thereby, ameliorating or preventing the discomfort resulted from the disturbance of bile acid metabolism.

The detailed technology and the preferred embodiments implemented for the present invention will be described in the following paragraphs for people skilled in the field to appreciate the features of the claimed invention.

BRIEF DESCRIPTION OF THE DRAWINGS

The patent application contains at least one drawing executed in color. Copies of this patent document with color drawing(s) will be provided by the Office upon request and payment of the necessary fee.

FIG. 4A and FIG. 4B show a pathological dissection figure of the liver of mice in different feeding conditions, wherein FIG. 4A is a pathological dissection figure of the liver, and FIG. 4B is a picture before dissection. Group A is provided with a normal diet, group B is provided with a high-fat-diet, group D is provided with a high-fat-diet and daily administered with 100 mg/kg gallic acid.

DETAILED DESCRIPTION OF THE INVENTION

Figure 1:
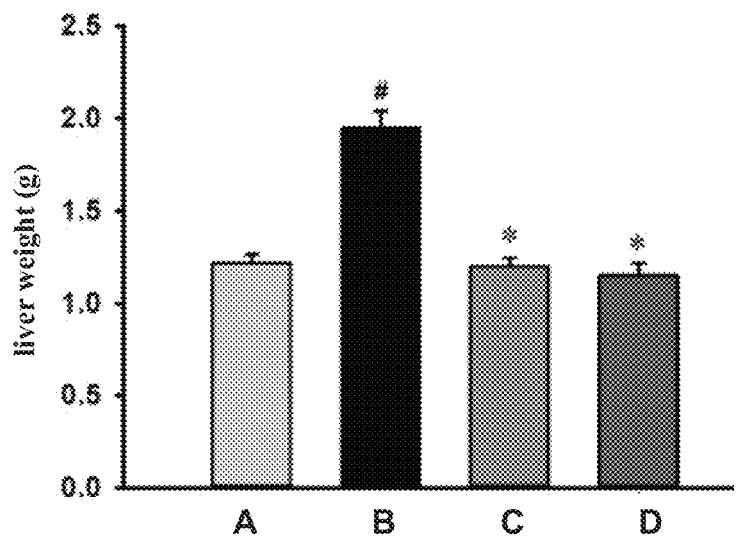
FIG. 1 shows the liver weight of the mice in different feeding conditions, wherein the horizontal axis represents the liver weight. Group A is provided with a normal diet, group B is provided with a high-fat-diet, group C is provided with a high-fat-diet and daily administered with 50 mg/kg gallic acid, and group D is provided with a high-fat-diet and daily administered with 100 mg/kg gallic acid.

Unless otherwise defined, the technical and scientific terms described herein have the same meaning as commonly understood by those skilled in the art.

The term "alleviate" or "alleviating" herein represents the effect of reducing, making less severe, or eliminating a condition and/or its symptom(s). The term "disturbance of metabolism" herein represents the metabolic abnormality in a subject caused by diseases or congenital genome defects. The term "treat" or "treating" includes the prevention of particular diseases and/or disorders, the amelioration of particular diseases and/or disorders, and/or the prevention or elimination of the diseases and/or disorder. For example, the term "treating diabetes mellitus" refers to changing the concentration of blood glucose toward a normal value, and increasing or reducing the value of blood glucose depending on the provided situation.

The term "become normal" herein refers to reducing the degree of deviation of a characterization of a subject from normal value. The term "effective amount" or "pharmacologic effective amount" refers to a dosage which is non-toxic and sufficient to provide a desired effect, and may vary depending on the age of administered subject, the situation and the administration route. Therefore, the "effective amount" could not be defined certainly and precisely. However, the "effective amount" that is administered to different subjects can be decided by those skilled in the art based on experience.

Unless otherwise clearly indicated, as used herein, the singular forms "a," "an," and "the" are intended to include the singular and plural forms. For example, as "a sample" would include a plurality of the sample and the equivalents known by those skilled in the art. In addition, "about", "approximately" or "almost" as used herein substantially represents within ±20% of the stated value, preferably within ±10% and more preferably within ±5%.

The present invention provides a method for alleviating at least one of the disturbance of bile acid metabolism, the disturbance of amino acid metabolism, and the disturbance of gut microbiota metabolism in a subject, comprising administering to the subject a composition comprising an active component.

The active component of the present invention is preferably selected from gallic acid, a pharmaceutically acceptable salt of gallic acid, a pharmaceutically acceptable ester of gallic acid, and combinations thereof. Gallic acid has the following chemical structure:

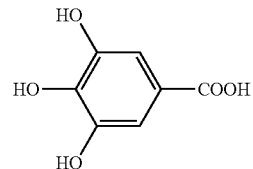

Any pharmaceutically acceptable salt of gallic acid could be used in the present invention, including pharmaceutically acceptable salts formed from gallic acid and an organic or inorganic base. The salts formed from inorganic bases include, but is not limited to, alkali mental salts (such as sodium salts and potassium salts), alkaline-earth metal salts (such as calcium salts and magnesium salts), transition metal salts such as ferric salts, zinc salts, copper salts, manganese salts and aluminum salts) and ammonium salts. Examples of the organic bases include, but are not limited to, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylene diamine, glucosamine, methylglucamine, theobromine, purine, piperidine, N-ethylpiperidine, tetramethylammonium compound, tetraethylammonium compound, pyridine, N,N-dimethylaniline, N-methylpiperidine, N-methylmorpholine, dibenzyl amine, N,N-benzylphenylethyl amine, 1-ephenamine, N,N'-benzylethylene diamine, polyamine resin and the like.

In addition, any pharmaceutically acceptable ester of gallic acid can be used in the present invention. The term "pharmaceutically acceptable ester of gallic acid" includes the ester obtained from the reaction between gallic acid and an acid, and the ester salt provided by a further reaction between the obtained ester and the above described organic or inorganic base. For example, a corresponding pharmaceutically acceptable ester can be provided by reacting gallic acid with hydrochloric acid, hydrobromic acid, sulfuric acid, sulfamic acid, nitric acid, phosphoric acid and the like, or an organic acid such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citrate acid, digluconic acid, ethanesulfonic acid, glutamine, glycolic acid, glycerophosphoric acid, hemisulfic acid, hexanoic acid, formic acid, 2-isethionic acid, lactic acid, hydroxymaleic acid, malic acid, malonic acid, mandelic acid, mesitylenesulfonic acid, methanesulfonic acid, naphthalenesulfonic acid, nicotinic acid, 2-naphthalene sulfonic acids, oxalic acid, pamoic acid, pectinic acid, phenyl acetic acid, 3-phenylpropionic acid, pivalic acid, propionic acid, pyruvic acid, salicylic acid, stearic acid, succinic acid, sulfanilic acid, tartaric acid, p-toluenesulfonic acid, or undecanoic acid. Subsequently, the obtained ester is further reacted with a suitable organic or inorganic base indicated above to form a corresponding ester salt.

The inventors of the present invention found that gallic acid is effective in alleviating the disturbance of bile acid metabolism, the disturbance of amino acid metabolism and the disturbance of gut microbiota metabolism in a subject in disease. Therefore, the composition involved in the present invention can be used for alleviating at least one of the disturbance of bile acid metabolism, the disturbance of amino acid metabolism and the disturbance of gut microbiota metabolism.

In particular, the inventors of the present invention found that gallic acid can effectively alleviate the disturbance of bile acid metabolism and make the metabolism of bile acid in body become normal. It has been known that the disturbance of bile acid metabolism is related to cholestasis liver diseases, cholestasis, bile duct infection, bile duck stones, and congenital bile duct diseases. Therefore, it is believed that the composition involved in the present invention can be used for treating the cholestasis liver diseases, cholestasis, bile duct infection, bile duck stones and/or congenital bile duct diseases.

Gallic acid can effectively alleviate the disturbance of amino acid metabolism and make the metabolism of amino acid in body become normal. It has been known that the disturbance of amino acid metabolism is related to hypertension, hyperlipidemia, atherosclerosis, diabetes, and tumor. Therefore, it is believed that the composition involved in the present invention can be used for treating hypertension, hyperlipidemia, atherosclerosis, diabetes and/or tumor.

Furthermore, gallic acid can effectively alleviate the circumstance of the disturbance of gut microbiota metabolism. It has been known that the disturbance of gut microbiota metabolism is related to the aging, inflammatory enteritis, depression disorder, anxiety disorder, immune disorder, and allergy. Therefore, it is believed that the composition involved in the present invention can be used for treating aging, inflammatory enteritis, depression disorder, anxiety disorder, immune disorder, allergy, etc.

It is preferred that gallic acid is used as the active component to provide the composition involved in the present invention.

The composition involved in the present invention can be prepared in any suitable form and be administered by any suitable route. For example, the composition can be administrated by oral administration, subcutaneous injection, intravenous injection, etc, but is not limited thereby.

Taking the manufacture of a composition suitable for oral administration as an example, the composition may comprise a pharmaceutically acceptable excipient and/or carrier which has no adverse effect on the desired activity of gallic acid and/or a pharmaceutically acceptable salt and/or ester of gallic acid. Examples of a suitable excipient include, but is not limited to, water, a salt solution, a vegetable oil, polyethylene glycol, gelatin, amylose starch, lactose, magnesium stearate, talcum, silicic acid, viscous paraffin, fatty acid monoglycerides, glycerol, fatty acid ester, hydroxyl methyl cellulose, and vinylpyrrolidone. Examples of a suitable carrier include, but are not limited to a solution, an emulsifying agent, a suspending agent, a decomposing agent, a binding agent, a stabilizing agent, a chelating agent, a diluting agent, a gelling agent, an antiseptic agent, a lubricant agent, a surfactant, an adjuvant, and the like, or other carriers suitable for the present invention. Examples of a form suitable for oral administration include a tablet, a capsule, a granule, a powder, a fluidextract, a solution, syrup, a suspension, an emulsion, and a tincture.

As for a composition suitable for subcutaneous injection or intravenous injection, the composition may comprise one or more components such as an isotonic solution, a saline buffer solution (e.g., a phosphate buffer or a citric acid salt buffer), a solubilizer, an emulsifier, and other carriers to manufacture the composition as an intravenous injection, an emulsion intravenous injection, a powder injection, a suspension injection, or a powder-suspension injection.

The composition may optionally comprise other additives, such as a flavoring agent, a toner, a coloring agent, etc. to enhance the taste and visual appeal of the resultant composition. To improve the storability of the resultant composition, the composition may also comprise a suitable amount of a preservative, a conservative, an antiseptic, an anti-fungus reagent, etc.

The composition involved in the method of the present invention may comprise an effective amount of gallic acid and/or its pharmaceutically acceptable salt and/or ester. The composition may also comprise one or more other active components to further enhance the efficacy of the method of the present invention or to increase the application flexibility and adaptability for the method, as long as the other active components have no adverse effect on the gallic acid and/or its pharmaceutically acceptable salt and/or ester. In addition, the composition can be applied with various administration frequencies, such as once a day, several times a day or once for days, etc. Depending on the requirements of the subject, the dosage of the composition can be adjusted. For example, for patients with acute conditions, the dosage can be increased to several times or several tens of times, depending on the practical requirements.

The present invention also provides a method for alleviating at least one of the disturbance of bile acid metabolism, the disturbance of amino acid metabolism, and the disturbance of gut microbiota metabolism in a subject, comprising administering to the subject a health food comprising an active component selected from the group consisting of gallic acid, a pharmaceutically acceptable salt of gallic acid, a pharmaceutically acceptable ester of gallic acid, and combinations thereof. The pharmaceutically acceptable salt and ester of gallic acid are all as described hereinabove. The health food can be prepared as a form of a solid, a liquid or a suspension. For example, it can be prepared as a form suitable for daily use, such as a food, a drink, a health food, an additive, etc., for the long-term use for ordinary users or patients, thereby achieving the effects of daily health care, or alleviating at least one of the disturbance of bile acid metabolism, the disturbance of amino acid metabolism, and the disturbance of gut microbiota metabolism. It is preferred that the health food contains gallic acid. The health food may especially be used for controlling diseases related to the disturbance of bile acid metabolism, such as cholestasis liver diseases, cholestasis, bile duct infection, bile duck stones, congenital bile duct diseases, etc.

The present invention will be further illustrated in details with specific examples as follows. However, the following examples are provided only for illustrating the present invention, and the scope of the present invention is not limited thereby.

EXAMPLES

In this experiment, 8-weeks-old and 20 to 25 g C57BL6/J male mice were divided into four groups (10 mice in each group), wherein the first group was a normal group (control), the second group was a high-fat-diet group, the third group was a high dosage of gallic acid treated group, and the fourth group was a gallic acid treated group at a low dosage. The gallic acid is purchased from Sigma, U.S.A.

The mice were fed with a normal diet or a high-fat-diet, wherein the nutritional ingredients are shown in Table 1. In the first group, the mice were fed with the normal diet ad libitum; in the second group, the mice were fed with the high-fat-diet (contain of 60% fatty acid) ad libitum; in the third group, the mice were fed with the high-fat-diet ad libitum and orally administered with gallic acid daily at a dosage of 100 mg/kg; and in the fourth group, the mice were fed with the high-fat-diet ad libitum and orally administered with gallic acid daily at a dosage of 50 mg/kg. In addition, to ensure experimental stability, the mice in the first and second group were given water at a volume the same as that in the third and fourth group. At the age of 16-week-old, the urine of the mice was collected, and the concentration of the blood glucose and serum insulin were measured. Then, the mice were sacrificed, and the serum was collected for the analysis of metabolic markers. The liver was weighted and photographed.

TABLE 1

The nutritional ingredient in different diet

| Diet | carbohydrate (%) | fat (%) | protein (%) |
|---|---|---|---|
| normal diet (calorific capacity: 4.14 kcal/g) | 58.5 | 12.7 | 28.8 |
| high-fat-diet (calorific capacity: 5.24 kcal/g) | 20.0 | 60.0 | 20.0 |

Figure 2:
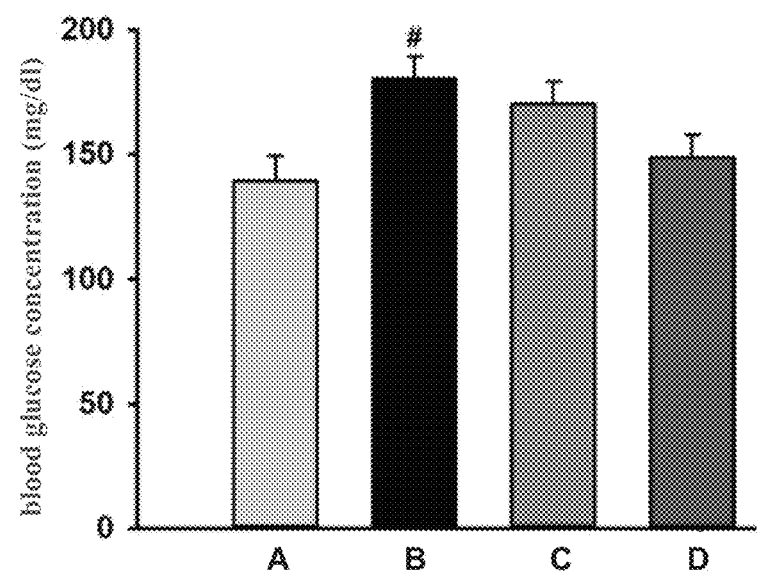
FIG. 2 shows the concentration of blood sugar of the mice in different feeding conditions, wherein the horizontal axis represents the concentration of blood sugar. Group A is provided with a normal diet, group B is provided with a high-fat-diet, group C is provided with a high-fat-diet and daily administered with 50 mg/kg gallic acid, and group D is provided with a high-fat-diet and daily administered with 100 mg/kg gallic acid.
Figure 3:
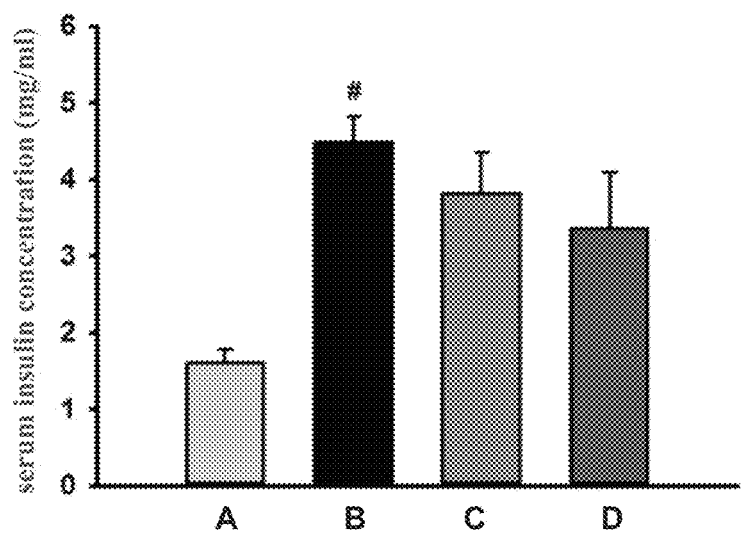
FIG. 3 shows the concentration of serum insulin of the mice in different feeding conditions, wherein the horizontal axis represents the concentration of serum insulin. Group A is provided with a normal diet, group B is provided with a high-fat-diet, group C is provided with a high-fat-diet and daily administered with 50 mg/kg gallic acid, and group D is provided with a high-fat-diet and daily administered with 100 mg/kg gallic acid.
Figure 4A:
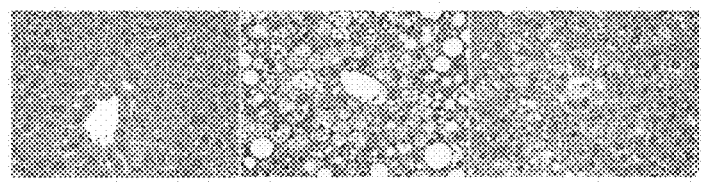
Figure 4B:
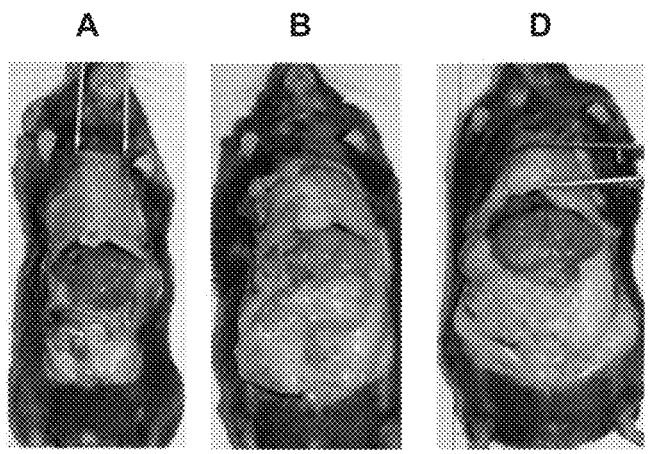

The liver weight, the blood glucose concentration, the blood serum concentration and the pictures of liver photograph are shown in FIGS. 1, 2, 3, 4A and 4B respectively, wherein "A" is the group treated with a normal diet (the first group), "B" is the group treated with a high-fat-diet (the second group), "C" is the group treated with a high-fat-diet and 50 mg gallic acid daily (the fourth group), and "D" is the group treated with a high-fat-diet and 100 mg gallic acid daily (the third group). As shown by the figures, as compared to the group treated with a high-fat-diet, gallic acid has the effects of ameliorating the nonalcoholic fatty liver and insulin resistance in mice induced by the high-fat-diet. The results indicate that gallic acid has an effect of ameliorating metabolic diseases.

The collected blood and urine were analyzed by a nuclear magnetic resonance spectrum. The steps are shown as follows.

(1) Urine: The urine (500 µl), PBS (50 µl) (81:19 vol/vol, comprising 0.2 M NaHPO$_4$ and 0.2 M NaH$_2$PO$_4$, pH=7.4), 10% deuteroxide, and 0.03% trimethylsilyl propionate (TSP) were mixed in a micro-centrifuge tube and centrifuged with 13000 rpm for 20 minutes at 4° C. The supernatant (500 µl) was collected and analyzed by 600 MHz nuclear magnetic resonance (NMR, Bruker AVANCE 600AV) at 25° C. The 1D NOESY FID signal was transferred to a one-dimensional NMR spectrum of graphing through Fourier transform.

(2) Blood: The serum (250 µl) and deuteroxide (350 µl) were mixed in a micro-centrifuge tube and centrifuged with 13000 rpm for 20 minutes at 4° C. The supernatant (500 µl) was collected and analyzed. The metabolites in serum were analyzed by using NMR sequence CPMG.

1. The Analysis of Bile Acid

It has been known that the concentration of taurine and glycine can be used as markers of bile acid metabolism (see Miyazaki T, Matsuzaki Y (2012) Taurine and liver diseases: a focus on the heterogeneous protective properties of taurine. Amino Acids, which is entirely incorporated hereinto by reference). Therefore, the integrated area of the spectrum of glycine (chemical shift 3.56 ppm singlet) and the taurine (chemical shift 3.40 ppm triplet) in the blood and urine were analyzed. The results are shown in Table 2.

TABLE 2

| species | the first group | the second group | the third group | biological sample |
|---|---|---|---|---|
| glycine | 194.75 ± 23.23 | 101.43 ± 4.57# | 142.91 ± 10.60* | serum |
| glycine | 145.23 ± 5.28 | 239.26 ± 24.18# | 206.51 ± 8.45* | urine |
| taurine | 648.94 ± 40.34 | 881.24 ± 61.44# | 489.81 ± 125.78* | |

Unit: the normalized and transferred NMR signal × 10$^3$
represents a significant difference as compared with the normal group (p < 0.05)
*represents a significant difference as compared with the high-fat-diet group (p < 0.05)

As shown in Table 2, as compared with the high-fat-diet group, the concentration of glycine and taurine in the blood/urine in the gallic acid treated group (the third group) are significantly close to the concentration of the control (the first group). The results indicate that the gallic acid has an effect of alleviating the abnormal bile acid metabolism.

2. The Analysis of Amino Acid Metabolism

It has been known that the concentration of isoleucine, leucine, valine, glutamate, glutamine, tyrosine, phenylalanine, alanine, lysine, arginine and ornithine can be used as the markers of amino acid metabolism (see Rare Disease Diet Control Manual—amino acid metabolism, Foundation for Rare Disorders, pages 18, 22, 26-31, which is entirely incorporated hereinto by reference). Therefore, the integrated area of the spectrum of isoleucine (chemical shift 1.01 ppm dublet), the leucine (chemical shift 0.97 ppm triplet) and the valine (chemical shift 1.04 ppm doublet) in the serum were analyzed. The results are shown in Table 3.

TABLE 3

| species | the first group | the second group | the third group | biological sample |
|---|---|---|---|---|
| isoleucine | 57.13 ± 5.76 | 23.34 ± 2.18# | 32.29 ± 3.25* | serum |
| leucine | 144.56 ± 12.32 | 97.27 ± 1.94# | 109.28 ± 2.36* | |
| valine | 102.71 ± 10.55 | 56.78 ± 2.20# | 68.26 ± 3.46* | |
| glutamate | 46.13 ± 2.42 | 32.04 ± 1.24# | 39.50 ± 1.39* | |
| glutamine | 47.40 ± 5.84 | 26.61 ± 2.58# | 40.61 ± 3.88* | |
| tyrosine | 8.36 ± 0.87 | 3.60 ± 0.32# | 6.78 ± 0.85* | |
| phenylalanine | 8.59 ± 0.47 | 4.92 ± 0.26# | 6.44 ± 0.39* | |
| alanine | 127.00 ± 15.52 | 77.65 ± 7.19# | 96.11 ± 6.07* | |
| lysine | 77.58 ± 2.83 | 62.16 ± 2.45# | 74.93 ± 2.24* | |
| arginine | 37.92 ± 3.49 | 26.24 ± 0.80# | 30.08 ± 0.78* | |
| ornithine | 43.20 ± 11.90 | 29.78 ± 1.46 | 36.39 ± 1.45* | |

Unit: the normalized and transferred NMR signal × 10$^3$
represents a significant difference as compared with the normal group (p < 0.05)
*represents a significant difference as compared with the high-fat-diet group (p < 0.05)

As shown in Table 3, as compared with the high-fat-diet group (the second group), the concentration of the markers of amino acid metabolism in blood in the gallic acid treated group (the third group) are significantly close to the concentration of control group (the first group). The results indicate that the gallic acid has an effect of alleviating the abnormal amino acid metabolism.

3. The Analysis of Gut Microbiota Metabolism

It has been known that the concentration of isobutyric acid, butanoic acid, hippuric acid, dimethylamine and trimethylamine can be used as the markers of the gut microbiota metabolism and reflect the change of gut microbiota. Therefore, the integrated area of the spectrum of isobutyric acid, butanoic acid, hippuric acid, dimethylamine and trimethylamine in the blood and urine were analyzed. The results are shown in Table 4.

TABLE 4

| species | the first group | the second group | the third group | biological sample |
|---|---|---|---|---|
| isobutyric acid | 26.41 ± 2.26 | 17.16 ± 0.73# | 22.49 ± 1.55* | serum |
| butanoic acid | 187.32 ± 3.36 | 163.46 ± 5.24# | 187.08 ± 10.46* | urine |
| hippuric acid | 48.22 ± 2.32 | 7.87 ± 0.55# | 10.33 ± 0.90* | |
| dimethylamine | 250.44 ± 9.68 | 226.46 ± 8.75 | 197.9 ± 9.20* | |
| trimethylamine | 1737.64 ± 125.07 | 504.72 ± 61.46# | 269.21 ± 76.77* | | represents a significant difference as compared with the normal group ($p < 0.05$)
*represents a significant difference as compared with the high-fat-diet group ($p < 0.05$)

As shown in Table 4, as compared with the high-fat-diet group (the second group), the concentration of the marker of the gut microbiota in the gallic acid treated group (the third group) were significantly close to the concentration of the control group (the first group). The results indicate that the gallic acid has an effect of alleviating the gut microbiota metabolism. The above results indicate that gallic acid has a variety of biological activities in alleviating the disturbance of bile acid metabolism, the disturbance of amino acid metabolism and the disturbance of gut microbiota metabolism.

The above detail description is for exemplary; however, without departing from the spirit of the present invention, the present invention may be embodied in various embodiments and should not be limited to the embodiments described in the specification. The change and equivalent conduct without departing from the spirit of the present invention should be involved in the scope of the present invention.

BRIEF DESCRIPTION OF REFERENCE NUMERALS

A: treated with normal diet
B: treated with high-fat-diet
C: treated with high-fat-diet and daily administered with 50 mg/kg gallic acid
D: treated with high-fat-diet and daily administered with 100 mg/kg gallic acid

What is claimed is:

1. A method for alleviating a metabolism disturbance of gut microbiota themselves in a subject, comprising administering to the subject a composition comprising an active component selected from the group consisting of gallic acid, a pharmaceutically acceptable salt of gallic acid, and combinations thereof, wherein the active component is administered at an amount ranging from 50 mg (as gallic acid)/kg-body weight to 100 mg (as gallic acid)/kg-body weight per day.

2. The method according to claim 1, wherein the active component is gallic acid.

3. The method according to claim 1, wherein the metabolism disturbance of gut microbiota causes at least one disease selected from the group consisting of aging, inflammatory enteritis, depressive disorder, anxiety disorder, immune disorder, and allergy.

4. The method according to claim 3, wherein the active component is gallic acid.

5. The method according to claim 1, wherein the composition is a pharmaceutical composition.

6. The method according to claim 1, wherein the composition is a health food composition.

* * * * *